(12) United States Patent
Grunwald et al.

(10) Patent No.: US 7,708,940 B2
(45) Date of Patent: May 4, 2010

(54) PROCESS FOR THE STERILIZATION AND/OR GERM REDUCTION OF MOLD MATERIALS

(75) Inventors: Martin Grunwald, Pulheim (DE); Norbert Weber, St. Tönnis-Str. (DE); Birgit Esser, Grevenbroich (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 934 days.

(21) Appl. No.: 10/600,773

(22) Filed: Jun. 20, 2003

(65) Prior Publication Data

US 2004/0084812 A1    May 6, 2004

(30) Foreign Application Priority Data

Jun. 25, 2002    (DE) ................ 102 28 421

(51) Int. Cl.
A61L 2/08    (2006.01)
(52) U.S. Cl. ................................. 422/22
(58) Field of Classification Search ............ 422/22
See application file for complete search history.

(56) References Cited

U.S. PATENT DOCUMENTS

| | | | | |
|---|---|---|---|---|
| 4,025,482 A | * | 5/1977 | Hu | 524/530 |
| 4,033,774 A | | 7/1977 | Johnson et al. | 106/35 |
| 4,741,966 A | * | 5/1988 | Cavezzan | 428/447 |
| 4,952,618 A | * | 8/1990 | Olsen | 524/17 |
| 5,378,531 A | * | 1/1995 | Larson et al. | 442/1 |
| 5,540,876 A | | 7/1996 | Larson et al. | 364/479 |
| 5,718,577 A | * | 2/1998 | Oxman et al. | 433/37 |
| 5,804,620 A | * | 9/1998 | Amos | 524/99 |
| 5,849,812 A | | 12/1998 | Zech et al. | |
| 6,121,362 A | * | 9/2000 | Wanek et al. | 524/448 |
| 6,547,467 B2 | * | 4/2003 | Quintero | 401/132 |
| 6,998,427 B2 | * | 2/2006 | Del Torto et al. | 523/109 |

FOREIGN PATENT DOCUMENTS

| | | |
|---|---|---|
| DE | 1 745810 | 1/1970 |
| DE | 29 08 087 A1 | 2/1980 |
| DE | 37 24 243 A1 | 2/1989 |
| DE | 37 32 379 A1 | 4/1989 |
| DE | 38 38 587 A1 | 5/1990 |
| DE | 37 41 575 C2 | 6/1990 |
| DE | 197 19 438 A1 | 11/1997 |
| DE | 101 04 079 A1 | 8/2002 |
| EP | 0 164 190 | 12/1985 |
| EP | 0 173 085 B1 | 3/1986 |
| EP | 0 265 776 | 5/1988 |
| EP | 0 269 819 B1 | 6/1988 |
| JP | 52-13234 | 4/1977 |
| JP | 1138230 A | 5/1989 |
| JP | 6233783 A | 8/1994 |
| JP | 7-112910 | 5/1995 |
| JP | 7112910 A | 5/1995 |
| JP | 11139921 A | 5/1999 |
| JP | 11335223 A | 12/1999 |
| WO | WO 99/15132 | 4/1999 |
| WO | WO 00/07546 | 2/2000 |

OTHER PUBLICATIONS

The Condensed Chemical Dictionary, Van Nostrand Reinhold Company, Inc., pp. 403, 1981.*
Database WPI, Derwent Publications, Access No. 1975-26486W, XP-002252986.
Abstract of DE 19719438 from EPO website database.
EPO Search Report (in German), dated Sep. 1, 2003 for EP 03012768.

* cited by examiner

*Primary Examiner*—Elizabeth L McKane
(74) *Attorney, Agent, or Firm*—Norris McLaughlin & Marcus, PA

(57) ABSTRACT

The present invention relates to a process for the sterilization and/or germ reduction of impression material by means of radiation.

11 Claims, No Drawings

PROCESS FOR THE STERILIZATION AND/OR GERM REDUCTION OF MOLD MATERIALS

The present invention relates to a process for sterilization and/or germ reduction of impression materials.

Different types of impression materials are well known (see R. G. Craig, Restaurative Dental Materials, The C.V. Moosbe-Comp. St. Louis, Toronto, London, 1980, pp. 1979). Overall, very high requirements are set for these types of materials (compare K. Eichner, Zahnärztliche Werkstoffe und ihre Verarbeitung, Volume 1, A, Hüithig Verlag, Heidelberg, $4^{th}$ edition, 1981, pp. 45):

1. Pleasant smell, taste and aesthetic appearance.
2. The substances must not contain any toxic or irritating ingredients.
3. The substances must exhibit a storage stability of several months.
4. The substances must be economical in their production and result in a precise mold.
5. The substances must be easy to handle.
6. The hardening characteristics must match the clinical requirements.
7. The hardened substances must be elastic and must not produce lasting deformations on tensile load.
8. The cured substances must have sufficient resistance to pressure and must be break-resistant.
9. The cured substances must have dimensional stability at room temperature and normal humidity for such a period of time, so that exact plaster casts can be produced within an appropriate time frame.
10. The cured substances must not cause any plaster deterioration and must be compatible with other impression materials From the group of various materials, elastomer impression materials are especially advantageous, among other things because of their beneficial application-technical and mechanical properties as opposed to non-elastomer impression materials.

Various types of elastomer impression materials are known, as, for example, elastomers with polymer chain structures that set by means of additional reaction (as, for example, additional cross-linking silicone impression material (so-called A-silicone)), which by means of a hydroxylation reaction of vinyl groups on a polydiorganyl group containing polymer (vinyl polymer) react with a SiH group containing polydiorgano siloxane (SiH-cross-linker), and thereby form an elastomer, respectively corresponding polyether materials (as, for example, described in DE-A1-3741575, respectively DE-A1-3838587), or by means of condensation reaction, elastomer forming impression materials, as, for example, condensation cross-linking silicone impression materials (so-called C-silicones) or, however, polyether impression materials (as, for example, described in DE 101 04 079.2-42 and for example in the therein appreciated EP 0 269 819 B1). Other frequently used impression materials are those with polyether chains and cross linkage via aziridino groups (as, for example, described in DE-B-17 45 810); polyether impression materials are also known in acrylate—respectively methacrylate groups, for example from EP 0 173 085. These types of impression material essentially satisfy the previously stated properties for impression materials.

In general, these elastomer impression materials are provided as pastes before "setting" (i.e., formation of the elastomer structure), which generally consist of two components (frequently called base paste and catalyst or hardener paste) and set to (cross-link) the elastomer after mixing.

By means of a impression material, the negative imprint of a situation of the physical geometry is produced in the previously mentioned fields of application, for example for the production of a replacement part or for diagnostic reasons, or, however, a stamp material is produced. Thereby the situation is to be reproduced in as much detail as possible. This means, that for this reason especially elastomer impression materials are recommended, which not only exhibit a high accuracy of detail and dimensional stability even when the mold is being stored, but which also can be well disinfected without major changes of the physical properties, which is of importance when applied in the medical field in as far as the molded body parts exhibit a more or less intensive germ population, which may result in contamination with these germs in subsequent work processes, such as model making, preparation of the restorative work etc., and may ultimately substantially endanger the persons working on these molds and on the replacement parts that are being produced with the help of these molds. Many processes for the disinfection of cured molds therefore exist (for example, by means of $H_2O_2$ UV-radiation, application of disinfecting agents (for example in F. M. Blair, R. W. Wassell, British Dental Journal, Vol. 180, No. 10, 1996, pp. 369, respectively G. L. Adabo, E. Zanarotti, R. G. Fonseca, C. A. Cruz, Journal of Prosthetic Dentistry 81 (5), 1999, pp. 621) or y-ray sterilization of molds (for example, in J. Setz, U. Benzing, Deutsche Zahnärtzliche Zeitschrift, 44, 1989, pp. 106)). All these processes are, however, performed on the already "cured", i.e., the elastomer molds.

In the previously mentioned medical fields of application, however, the problem frequently arises during the molding procedure, in that the impression material in the not-yet-cured, respectively not in the cross-linked condition, comes into contact with injured skin or mucous membranes or osseous tissue (for example, through bleeding of the mucous membrane, when taking dental molds, respectively when taking molds when implants are being placed, or when taking molds on not-yet-healed skin tissue, when taking molds within the framework of epithetic care or in skin molds).

The danger naturally exists that these body parts that come into contact with the impression material are being contaminated with germs (as, for example, bacteria, bacilli, fungi, yeasts, viruses) from the impression material, or from the primary packaging agent, or from the accessories needed for the application (as, for example, cannulas for mixing of impression material, which are provided in twin-chamber cartridges, or mixing spatulas); this germ contamination can lead to severe health problems that may have especially negative effects on persons with limited immune system function.

Furthermore, it is desirable in the so-called stamp technique (as described in their fundamental basics among others in Y. Xia, G. M. Whitesides, and Angew. Chem. Int. Ed. 1998, 37, 550-575; E. Delamarche, H. Schmid, B. Michel, H. Biebuyck, Adv. Mater, 1997, 9, 741-746; H. Schmid, B. Michel, Macromolecules 2000, 33, 3042-3049), in which substrates or structures are transferred to surfaces by means of stamps, that these stamp materials be germ-free, especially in the case when biologically or pharmaceutically active materials are transferred by means of this technique. In this case, the subsequent disinfection of the (repeatedly used) stamp can, by its nature, is not admissible (since residue of disinfection agents are thereby transferred into the biological substrate and can influence the biological functions), just as the admixture of antimicrobially active substances into the stamp material (which can just as well be transferred into the biological substrate, or may cause a surface inactivation of the biological substrate).

There has therefore been no lack of experiments to take steps to eliminate this danger of germ infestation.

Thus, a procedure has been described by D. N. Firtell, D. J. Moore, G. B. Pellen, Jr. in Journal of Prosthetic Dentisty, 1972, pp. 419-422, designed to sterilize alginate powder means of ethylene oxide gasation. This suitable method for pulverized materials can, however, not be transferred to impression material pastes with an easy procedure.

There was also an attempt to produce a low germ or even sterile mold by the addition of germ killing agents to the impression materials, in that the germ growth-prohibiting agent was added to the materials (for example DE 37 24 243, JP 07112910, WO 99/15132, WO 00/07546). In this form of problem solving, there exists the danger of a change of the properties of the thus-equipped impression materials, and above all, all the respective additives bring the disadvantage that through them, the respective body part is also contaminated along with all the disadvantages this entails, such as localized irritations to potential basic intolerance, or allergic reactions through the active ingredients. Furthermore, antimicrobially active agents in general have a limited action function on specific germs. As already explained, such a procedure is prohibitive in the application of the so-called stamp technique.

In U.S. Pat. No. 4,033,774, a thermoplastic, not an elastomer dental impression material, is being described that supposedly can be sterilized in an autoclave before usage, without any further details being given in this context. A generally applicable solution to the problem for possible germ reduction in elastomer impression materials is not thereby described.

The usage of a radiation sterilized mold spoon and a radiation sterilized mixing cannula for a impression material in a cartridge is described by Th. Kaus, A. Sethi in ZWR, 110th year of publication, 2001, pp. 22-26, however, not the usage of a sterilized impression material.

An example of γ-radiation treatment of plastics applicable in the dental field is presented with JP 52013234 B4, whereby a severe change in elasticity of a plastic that can be used in the dental field, through γ-radiation of polymethyl methacrylate powder is being described. This described material is not usable as impression material and the subject of germ reduction is not addressed.

U.S. Pat. No. 5,540,876 describes a thermoplastic, non-elastomer, γ-radiation-treated poly (epsilon-caprolactone) and its change in properties through γ-radiation treatment, which makes the material usable in the application for dental techniques; this material is not usable as elastomer impression material.

The conclusion must therefore be drawn that, according to the current state of the art, no generally applicable process for the production of a germ-reduced or sterile impression material or substance for the preparation of a stamp, which is provided in this low-germ form prior to taking the mold, or prior to producing the stamp, is known.

The invention is based on the task of stating a process for the safe reduction of germs in impression materials.

This task is solved according to the invention through the features described herein. In its broadest aspects, the present invention relates to a process for the sterilization and/or germ reduction of impression materials and/or their components, wherein the impression materials and/or their components are subjected to radiation sterilization. According to the invention, the process is used in the medical field, especially in the dental field, in otoplasty, orthopedics, epithetics, defect surgery, in the area of molds in otorhinolaryngology, veterinary medicine or the molds of skin parts, as well as stamp material for stamp techniques, especially in the application of biological or pharmaceutical substrates. It could be determined that impression materials, especially for the application in the previously-mentioned medical fields and/or as stamp material in the so-called stamp techniques, especially prior to cross-linking by means of high-energy radiation, preferably through gamma radiation, respectively electron radiation (β-radiation), can be germ-reduced or sterilized. The term radiation sterilization is meant to designate germ reduction, as well as sterilization.

Considering the changes in properties (radiation cross-linking, degradation of polymer structures) described, for example, in JP 52013234 B4 and U.S. Pat. No. 5,540,876, this was not to be expected. For high radiation doses, degradation and recomposition mechanisms of the polydimethyl siloxane chains partially used in previously stated impression materials are known (D. J. T. Hill, C. M. L. Preston, A. K. Whittaker, S. M. Hunt, Macromol, Sym. 156, 95-102 (2000)). Against the background of potential radiation cross-linking, as described, for example, in W. Noll, Chemie und Technologie der Silicone, Verlag Chemie, Weinheim, $2^{nd}$ edition, 1968, page 199), such lasting properties of the respective silicone impression materials were not to be expected.

Sterilizations by means of radiation are essentially known (for example, in K. H. Wallhäuser, Praxis der Sterilisation—Desinfektion—Konservierung—Keimidentifizierung—Betriebshygiene, $3^{rd}$ edition, Georg Thieme Verlag, Stuttgart—New York, 1984, chapter 3.4), without the respective prior sterilization of the impression materials for the previously stated purposes.

The principles of γ- and β-ray sterilization are described in detail in the above mentioned monograph by K. H. Wallhäiuser, or other monographs.

Electron ray sterilization is performed by means of electron accelerators that bombard the accelerated electrons onto the material to be sterilized and thus have a high dosage effect on it within a short period of time. As a disadvantage in comparison to sterilization with γ-rays, which therefore must be considered especially advantageous, is the obviously lower penetration of the β-rays, so that the radiation with β-rays entails economic disadvantages compared to the γ-radiation because of the problems of sterilizing the previously mentioned mold or stamp substances in large quantities (and the associated necessity to sterilize the packages with the material in layers with only thin thickness).

The capacity for penetration in gamma radiation treatment is comparatively higher. In gamma radiation treatment, the piece to be sterilized is passed by a radiation source, generally an encased isotope $^{60}Co$, until the desired dose is reached. The higher penetration capacity of the γ-ray sterilization has the effect that the substances to be sterilized can be sterilized in larger units.

The treatment techniques with γ- or β-rays are generally known.

Depending on the radiation dose, different germ reduction rates can be achieved, which, however, are also dependent on the germs present in the germ population. Frequently 25 kGy are used in the radiation sterilization of medical products (compare previously mentioned monograph by K. H. Wallhäuser, page 233). Especially with impression materials or materials for stamp techniques, the radiation dose may be further reduced since the original germ level can be considered to be low due to hygiene measures at the company during the production processes (frequently medium bio burden of 5-10), in order to have a sufficient probability of "sterility" (i.e., the probability of finding a product containing germs is smaller than 1:1 million) guaranteed (notes thereto can be found in table B1 of ISO 11137: 1995 (E)), so that 20 kGy should be sufficient as a radiation dose.

Low radiation doses, which do not yet guarantee a safe sterility, can at least effect a substantial germ reduction. Depending on the bio burden and depending on the set goals (germ reduction, sterility), the radiation dose can be determined.

Basically, all types of impression materials, which are applied in the mentioned medical fields, or as stamp material, can be germ-reduced or sterilized by radiation. Preferred are the following cross-linking elastomer impression materials and especially preferred are the elastomer impression materials on the basis of cross-linkable polyether, or polysiloxane polymer skeletons.

Within this context, it is important that only minor changes of the physical or application-technical properties occur on the irradiated material compared to untreated material.

Surprisingly, it was determined that polyether impression materials and condensation cross-linking silicone impression materials exhibit no application-relevant changes, even in comparatively high radiation doses, such as 40 kGy. Notably, additional cross-linking silicon impression materials with polydimethyl siloxane polymer skeleton are more sensitive at higher radiation doses of, e.g., 40 kGy; hereby a cross-linking occurs (radiation cross-linking of the vinyl groups) that limits usability. Even with lower radiation doses, pre-cross-linkings appear in added cross-linking silicone impression materials, which consequently also appear in faster cross-linking kinetics. This means, although it is possible with the regular added cross-linking silicone impression materials on the basis of polydimethyl siloxane polymers, to sterilize them at suitable radiation doses and at still acceptable application-technical properties, however, the materials obtained this way exhibit distinct changes compared to the original materials. From G. G. Delidest, Radiat. Phys. Chem., 16, (1980), pp. 345-352; a "protective" effect of phenyl groups on the behavior of irradiated dimethyl diphenyl siloxanes is the known art. Similar statements can also be found in W. Noll, Chemie und Technologie der Silicone, Verlag Chemie, Weinheim, $2^{nd}$ edition, 1968, pp. 407 and 447.

Notably, it was discovered that the usage of phenyl group containing and vinyl group containing polydimethyl siloxane polymers in added cross-linking silicone impression materials results in considerably fewer changes, so that it is preferable to apply siloxane polymers with at least 3 Mol-%, preferably at least 10 Mol-%, on diphenyl siloxane and/or methyl phenyl siloxane units.

Other types of impression materials, such as alginate impression material powder, can also be sterilized by means of high-energy radiation. The changes observed in alginate impression materials indicate a partial chain-decomposition (viscosity reduction), which, however, has only a minor influence on the observed cross-linking kinetics, whereby the changes in viscosity can be counteracted by variations of the (powder: liquid- ratio.

This means that for each type of impression material, the maximum radiation doses resulting from physical or application-technical changes of properties can be determined by taking into consideration the original germ infestation and the desired degree of germ reduction. For the regular two-component impression materials cross-linking to an elastomer, or stamp substance on the basis of polyether or silicone polymer, a maximum radiation dose of 40 kGy is preferred, especially preferred is a maximum radiation dosage of 30 kGy.

It is advantageous to sterilize these mold or stamp substances in the primary packaging agent, and it is also especially advantageous to sterilize the accessories necessary for mixing and the application (whereby it is also feasible that from the exterior, the primary packaging agent, or the accessories (such as mixing spatula, mixing nozzles etc.) are also germ-reduced or sterilized by another method (for example sterilization by means of ethylene oxide, low-temperature plasma sterilization with $H_2O_2$ or similar methods)).

Sterilization by γ- or β-radiation of the material in the primary packaging agent and necessary accessories in a sealed end-package (for example, a seam-welded bag) is advantageous; especially advantageous is a twin-chamber cartridge as a primary packaging agent and mixing nozzles (mixing tips) as accessories. It is especially advantageous to provide germ-reduced or sterile mold or stamp substances in the primary packaging agent, in addition to the accessories, in an amount sufficient for a one-time application.

In this case, care should be taken that the used packaging agent, the accessories, and the foils or re-packaging materials, can tolerate the sterilization conditions of high-energy radiation. Such radiation sterilization stable packaging or accessories are quite well known.

Additionally, care should be taken when selecting primary packaging agents and accessories, so that the materials used exhibit sufficient stability versus the respective types of impression material.

Preferred embodiments of the present invention include the following embodiments utilized separately or in combination:

1. Two-component impression materials, which are cross-linked into an elastomer material, are used.
2. Additional condensation or via (meth)acrylate groups cross-linkable silicon impression materials, or addition, condensation, or via ring opening or (meth)acrylate groups cross-linkable polyether impression materials are used.
3. Impression materials which can be handled as a system (powder: fluids) are used.
4. An alginate mold substance (powder: water) is used.
5. An additional cross-linking silicon mold material is used, which contains in the formulation vinyl group containing polysiloxanes with at least partially present diphenyl siloxane- and/or phenyl methyl siloxane structural units.
6. Polymers are used, which contain at least 3 Mol-%, preferably at least 10 Mol-% diphenyl siloxane and/or phenyl methyl siloxane units.
7. The impression material and/or its components are sterilized in a primary packaging unit.
8. The impression material and/or its components are arranged in the primary packaging and are simultaneously treated with the accessories for mixing or for the application of the impression material.
9. A twin-chamber cartridge is used as primary packaging and a mixing nozzle as accessory.

10. The radiation sterilization is performed by means of gamma rays or electron rays.
11. A radiation dose of a maximum of 50 kGy, preferably 20 to 30 kGy, is used.
12. Application of the inventive process for impression materials used in the medical field.
13. Application of the inventive process for impression materials used in the dental field, in orthopedics, in otoplasty, in epithetics, defect surgery, veterinary medicine, in the field of molding in ENT-medicine or for the molding of skin parts.
14. Application of the inventive process for impression materials for the production of stamps for the transfer of structures, especially of biological and/or pharmaceutically active substrates.

The following examples are designed to describe the invention without limiting it.

EXAMPLE 1

In these tests, various types of impression materials (silicone impression material (condensation cross-linking), polyether impression materials (condensation cross-linking, or ring opening cross-linking)) are irradiated in twin-chamber cartridges with gamma rays of 25 kGy, and thereafter examined in comparison to the untreated samples. The results are compiled in the following table and show good stability of the examined types of impression material. All changes in the kinetics and viscosity that are due to the radiation treatment are also in a very acceptable range from an application-technical point of view.

Results of the Test Comparisons of Non-sterilized Compared to Sterilized Samples in a γ-radiation of 25 kGy.

| | Material | | | | | |
|---|---|---|---|---|---|---|
| | Aziridino polyether Impregum Garant L Duo Soft (2:1) | | Condensation cross-linking polyether impression material URH 0234-1/URH 0234-2 (4:1) | | Silicone impression material (condensation cross-linking) Xantopren Comfort Medium (4:1) | |
| | untreated | Irradiated | untreated | irradiated | untreated | irradiated |
| Viscosity basis [Pas] | 84 | 86 | 85 | 71 | 24 | 26 |
| Viscosity catalyst [Pas] | 249 | 220 | 90 | 76 | 3 | 3 |
| Processing time according to OSC-method [min] | 2.45 | 2.40 | 1.65 | 2.30 | 2.60 | 2.25 |
| Setting time according to OSC-method [min] | 3.50 | 3.50 | 2.75 | 3.65 | 3.85 | 3.55 |
| Reset after deformation [%] | 97.7 | 97.7 | 98.4 | 98.2 | 97.5 | 97.8 |

EXAMPLE 2

Various types of impression materials were subjected to a γ-radiation treatment at various doses of γ-radiation and the irradiated and non-irradiated ("O-samples") impression materials were examined physically. The results can be found in the following table. It is to be noted, that polyether impression materials (both, ring opening via an aziridino group, as well as cross-linking by condensation reaction) retain good application properties after radiation at 20 kGy as well as at 40 kGy. This also applies to condensation cross-linking silicone impression materials.

In additional cross-linking, silicone impression materials increases in viscosity occur by "pre-cross-linking" and concurrent pre-cross-linking kinetics acceleration, which are undesirable, even though the sample of Provil Novo Medium C.D.2 treated at 20 kGy results in a usable impression material despite the changes (with rubber properties after taking the mold, which have not exhibited any essential changes).

In the previously mentioned additional cross-linking silicone impression material "Provil Novo Medium C.D.2", SiH-cross-linkers are present next to polydimethyl siloxanes with terminal vinyl groups in the base paste. Separation of SiH-cross-linker and vinyl group containing siloxane polymers results in minor changes of viscosity, especially when diphenyl siloxane unit containing polymers are being used, which, however, still entail changes in the cross-linking kinetics and therefore do not present a general solution to the problem.

Radiation doses of 40 kGy on additional cross-linking silicone impression materials always lead to polymerization, and therefore result in an elastic-viscous behavior of the pastes, which makes usage impossible. It can therefore be recognized that additional cross-linking silicone impression materials behave more sensitively when sterilized with a high-energy radiation than other impression materials (without having to question the basic applicability of irradiated additional cross-linking silicone impression materials) and that an upper limit for the material-related toleration of radiation doses is hereby discernible.

Results of γ-radiation Tests at Various Radiation Doses With Different Types of Impression Materials

| | Material | | | | | | |
|---|---|---|---|---|---|---|---|
| | Polyether impression material ESPE Impregum Garant L Duo Soft, B: 007/C: 007 | B: URH 0246-4/ C: URH 0196-2 | Silicone impression materials Xantopren Comfort Medium, lot: 160182 | Provil Novo Medium* C.D. 2, Lot: 150352 | BER 083-2/BER 083-3* | BER 083/BER 083-1* |
| Cross-linking mechanism to the elastomer | Via aziridino groups | Condensation cross-linking | Condensation cross-linking | Additional cross-linking | Additional cross-linking | Additional cross-linking |
| Packaging agent | Twin-chamber cartridge, 2:1 | Twin-chamber cartridge, 4:1 | Twin-chamber cartridge, 4:1 | Twin-chamber cartridge, 1:1 | Twin-chamber cartridge, 4:1 | Twin-chamber cartridge, 4:1 |

*40 kGy: Basis and catalyst elastic-viscous, cannot be mixed
BER 083: Base paste consists of i.a. SiH-cross-linker, without vinyl oil;
BER 083-1: catalyst paste i.a. with polydimethyl siloxanes eith terminal vinyl groups and a viscosity of 1,000 mPas or 65,000 mPas
BR 083-2: Base paste consists of i.a. SiH-cross-linker, without vinyl oil;
BER 083-3: catalyst paste i.a. with vinyl oils of the general structure $H_2C{=}CH{-}Si(CH_3)_2{-}O{-}[Si(CH_3)_2{-}O]m{-}[Si(C_2H_5)_2{-}O]n{-}Si(CH_3)_2{-}CH{=}CH_2$ with each 3.0-3.5 Mol-% diphenyl siloxane units and a viscosity of 1,000 mPas or 60,000 mPas

| Dose | "O-sample" | 20 kGy | 40 kGy | "O-sample" | 20 kGy | 40 kGy | "O-sample" | 20 kGy | 40 kGy | "O-sample" | 20 kGy | "O-sample" | 20 kGy | "O-sample" | 20 kGy |
|---|---|---|---|---|---|---|---|---|---|---|---|---|---|---|---|
| Viscosity basis [Pas] | 84 | 77 | 78 | 43 | 42 | 43 | 25 | 27 | 31 | 60 | 164 | 45 | 26 | 43 | 22 |
| Viscosity catalyst [Pas] | 249 | 162 | 146 | 35 | 31 | 34 | 3 | 3 | 3 | 58 | 102 | 88 | 127 | 71 | 149 |
| Processing time after OSC-measurement [min] | 2.45 | 2.40 | 2.30 | 1.60 | 1.85 | 1.70 | 2.40 | 2.40 | 2.50 | 2.20 | 1.00 | 3.10 | 1.65 | 2.20 | Can't be measured |
| Setting time after OSC-measurement [min] | 3.50 | 3.40 | 3.30 | 3.25 | 4.05 | 3.60 | 3.95 | 4.03 | 4.23 | 3.00 | 2.30 | 4.20 | 3.25 | 3.10 | 2.55 |
| Reset after deformation [%] | 97.7 | 97.5 | 97.2 | 98.2 | 98.5 | 98.0 | 96.1 | 96.5 | 96.6 | 99.7 | 99.8 | 96.4 | 98.2 | 98.2 | 99.1 |
| Shore A-hardness 1 h | — | 52 | 52 | 40 | 39 | 38 | 39 | 40 | 42 | 56 | 55 | — | — | 62 | 63 |

EXAMPLE 3

The powder of an alginate impression material (Xantalgin Select) is sterilized at various radiation doses by means of gamma rays, and the physical core properties of the powders mixed with water are determined prior to and after the radiation treatment (see following table). This illustrates, that a kinetic change is caused by the γ-radiation that also entails an application-technically determinable degradation in viscosity (by chain degradation, which, however, can be partially compensated with the (powder:water-) ratio)). This also clarifies that at 40 kGy a no longer tolerable dosage is present for the provided alginate powder.

Results of the γ-ray Sterilization of Alginate Powder (Xantalgin Select)

16.8 g powder: 40 ml water; time in mouth 1.5 min each

|  | Untreated sample ("O-sample") | Irradiated at 20 kGy | Irradiated at 40 kGy |
|---|---|---|---|
| Processing time (OSC) [min] | 1.40 | 1.60 | 2.40 |
| Setting time (OSC) [min] | 1.75 | 2.00 | Can no longer be evaluated in the same way |
| Setting time "rod test" (OSC) [min] (non-sticking-test) | 2.00 | 2.10 | 2.10 |

At radiation doses of 20 or 40 kGy, irradiated alginates are thin-flowing compared to the "O-sample" with the same (powder:water-) ratio.

EXAMPLE 4

In this test series, changes of additional cross-linking two-component silicone impression materials are tested regarding the change in properties with gamma ray sterilization at 25 kGy compared to non-sterilized samples. Thereby variant BER 091-12/093-13 is a variant, which, regarding the vinyl group containing polymers, is constructed of two polydimethyl siloxanes with two terminal vinyl groups each. These polymers exhibit viscosities of about 1000 mPas or 6500 mPas. Variant BER 091-4/091-5 instead contains corresponding vinyl group containing polymers, which, next to the dimethyl siloxane units, also exhibit a content of 3.0-3.5 Mol-% diphenyl siloxane units.

In BER 091-10/091-1 a respective polymer from the firm, Wacker Chemie GmbH, is used with about 10 Mol-% phenyl methyl siloxane units. The respective data are shown in the enclosed table. As is to be expected, in γ-ray sterilization of BER 091-12/091-13, there is in turn an increase in viscosity with a concurrent cross-linking kinetic acceleration, which turns out to be considerably lower with the diphenyl siloxane containing polymer that is used in BER 091 4/091 5. The most negligent changes can be achieved with the polymer used in BER 091-10/091-11. That means that by the variation of the polymers that are used in the additional cross-linking silicone impression materials, the changes in consistence or kinetics can be purposefully influenced. Thus, the respective impression materials are optimized regarding their applicability after gamma ray sterilization.

Results of Various Additional Cross-linking Silicone Impression Materials Sterilized by Means of γ-ray Sterilization at 25 kGy (For Comparative Purposes Non-sterilized):

| BER | 091-4/091-5 | 091-10/091-11 | 091-12/091-13 |
|---|---|---|---|
| Viscosity basis [Pas] | 230 (100) | 25 (34) | 351 (72) |
| Viscosity catalyst [Pas] | 178 (154) | 86 (70) | 198 (132) |
| Processing time (OSC) [min] | 1.70 (3.10) | 2.25 (3.15) | 1.30 (3.10) |
| Setting time (OSC) [min] | 3.10 (4.20) | 3.25 (4.15) | 2.80 (4.35) |
| Reset after deformation [%] | 99.5 (99.6) | 99.4 (99.0) | 99.5 (99.5) |

* too fast
** too slow
091-4: 18.00% PDV 0331 (ABCR); 9.50% PVD 0346 (ABCR); 16% SiH-cross-linker; 55.5% filling agent; other set-up and structural agents
091-5: 7.50% PDV 0346 (ABCR); 36.00% PVD 0331 (ABCR); 55.4% filling agent; 80 ppm Pt as Pt-dvds-catalyst (related to the catalyst paste); other set-up and structural agents
091-10: 28.00% SLM 435064/10; 16% SiH-cross-linker; 54.7% filling agent; other set-up and structural agents
091-11: 42.00% SLM 435064/10; 56.4% filling agent; 80 ppm Pt as Pt-dvds-catalyst (related to the catalyst paste); other set-up and structural agents
091-12: 18.00% Silopren U1; 9.50% Silopren U65; 16% SiH-cross-linker; 55.5% filling agent; other set-up and structural agents
091-13: 36.00% Silopren U1; 7.00% Silopren U65; 55.4% filling agent; 80 ppm Pt as Pt-dvds-catalyst (related to the catalyst paste); other set-up and structural agents
Silopren U1, Silopren U65: Products of the company GE Bayer Silicones; polydimethyl siloxane with terminal vinyl groups on both chain ends
Dvds: 1,3-divinyl disiloxane
PDV 0331 (ABCR): viscosity 1000 mPas; MG: 27,000; 3.0-3.5 Mol-% diphenyl siloxane; with divinyl end groups
PDV 0346 (ABCR): viscosity 60,000 mPas; MG: 87,000; 3.0-3.5 Mol-% diphenyl siloxane; with divinyl end groups
SLM 435064 (Wacker): phenyl methyl siloxane units: approximately 10 Mol-%; with divinyl end groups; viscosity 600 mPas

EXAMPLE 5

The results of the germ count determination compiled in the following table shows, that after sterilization with gamma rays no fertile microorganisms can be determined any more. Results of the germ count determination according to DIN EN 1174-1, -2, ISO 11737-1:

| Material | Untreated sample Germ count bacteria [KBE/g] | Germ count, fungii, yeasts [KBE/g] | Treated with gamma rays Dose | Results of the sterility test |
|---|---|---|---|---|
| C-silicone Xantopren Comfort Medium | <10 | <10 | 25 kGy | No fertile Micro-organisms were determined |
| Polyether impression materials Aziridino polyether Impregum Garant L Duo Soft | <10 | <10 | 20 kGy | No fertile micro-organisms were determined |
| Condensation cross-linkable polyether impression material | <10 | <10 | 20 kGy | No fertile micro-organisms were determined |

-continued

| Material | Untreated sample Germ count bacteria [KBE/g] | Germ count, fungii, yeasts [KBE/g] | Treated with gamma rays Dose | Results of the sterility test |
|---|---|---|---|---|
| (URH 0246-4/ URH 0 196-2) Addition cross-linkable Silicone impression material BER 083-2/ 083-3 | <10 | <10 | 20 kGy | No fertile micro-organisms were determined |
| Alginate impression material Xantalgin Select | <10 | <10 | 20 kGy | No fertile micro-organisms were determined |

EXAMPLE 6

Electron ray sterilization tests on various types of impression material:

The following two tables show comparative data in regards to various types of impression materials in non-sterilized condition and after an electron ray sterilization with a dose of 25 kCy each. The examined electron-ray-treated samples did not exhibit any fertile microorganisms. Analogous to the results of the gamma ray treatment, condensation cross-linking silicone impression materials, respectively polyether or alginate impression materials, exhibit only minor influence on the physical properties. In another table there are examples of additional cross-linking silicone impression materials, whereby the variant BER 001-12/001-13 contains polydimethyl siloxanes with terminal vinyl groups as vinyl group each containing oils. The increase in viscosity is obvious, as is the concurrent kinetic acceleration, which, even after the radiation sterilization still carries silicone impression materials that can be handled easily. Even considerably fewer changes can be achieved with the PDV 0331/0346, respectively SLM 435064 in BER 091 4/091 5, respectively BER 091 10/091-11.

| Type of material | Silicone mold material, condensation cross-linking | | | Polyether impression material, condensation cross-linking | | | | | Alginate impression material | |
|---|---|---|---|---|---|---|---|---|---|---|
| Material | Xantopren Comfort Medium | | | URH 265-1/URH 234-2 | | | URH 260-1/URH 258-2 | | Alginoplast fast set | |
| | prior to sterilization | After electron ray sterilization | | Prior to sterilization | After electron ray sterilization | | Prior to sterilization | After electron ray sterilization | Prior to sterilization | After electron ray sterilization |
| Dose | — | 25 kGy* | | — | 25 kGy* | | — | 25 kGy | — | Powder irradiated at 25 kGy |
| Packaging agent | Twin-chamber cartridge, 4:1 | | | Twin-chamber cartridge, 4:1 | | | Twin-chamber cartridge, 2:1 | | Powder: fluid system | |
| Viscosity basis [Pas] | 16 | 21 | 116 | 104 | 112 | 114 | — | | — | |
| Viscosity catalyst [Pas] | — | 3 | 75 | 67 | 83 | 71 | — | | — | |
| Processing time (OSC-method) [min] | 2.25 | 2.15 | 1.57 | 1.93 | 1.50 | 1.70 | 1.10 | | 1.33 | |
| Set-time (OSC-method) [min] | 3.35 | 4.00 | 2.70 | 3.53 | 2.40 | 2.50 | 1.65 | | 2.40 | |
| Reset after deformation [%] | 98.1 | 98.2 | 99.0 | 98.9 | 98.7 | 98.4 | — | | — | |
| Non-stick-test [min] | — | — | — | — | — | — | 1.35 | | 1.55 | |

*fertile microorganisms could not be determined

Type of material  Silicone impression materials, additional cross-linking
Packacking agent  Twin-chamber cartridges 1:1
BER  091-4/091-5   BER 091/10/-11   091-12/091-13

| | Prior to sterilization | Electron ray-sterilized, 25 kGy | Prior to sterilization | Electron ray-sterilized, 25 kGy | Prior to sterilization | Electron ray-sterilized, 25 kGy |
|---|---|---|---|---|---|---|
| Viscosity basis [Pas] | 100 | 132 | 34 | 29 | 72 | 132 |
| Viscosity catalyst [Pas] | 154 | 183 | 70 | 80 | 132 | 152 |

-continued

Type of material   Silicone impression materials, additional cross-linking
Packacking agent   Twin-chamber cartridges 1:1
BER   091-4/091-5   BER 091/10/-11   091-12/091-13

| | Prior to sterilization | Electron ray-sterilized, 25 kGy | Prior to sterilization | Electron ray-sterilized, 25 kGy | Prior to sterilization | Electron ray-sterilized, 25 kGy |
|---|---|---|---|---|---|---|
| Processing time (handling test) [min] | 4.68 | 3.85 | 5.45 | 5.23 | 5.40 | 3.45 |
| Processing time (according to OSC-method) [min] | 3.10 | 2.50 | 3.15 | 2.80 | 3.10 | 2.10 |
| Set-time (according to OSC-method) [min] | 4.20 | 4.05 | 4.15 | 3.90 | 4.35 | 3.55 |
| Reset after deformation [%] | 99.6 | 99.05 | 99.0 | 98.2 | 99.5 | 99.7 |
| Bacteria count [KBE/g] | — | — | <10 | * | <10 | * |
| Fungii/yeast count [KBE/g] | — | — | <10 | * | <10 | * |

BER 091-12/-13: with Silopren U 1/U 65, i.e., polydimethyl siloxane with terminal vinyl groups of the viscosity 1 Pas, or 65 Pas
BER 091-10/-11: with SLM 435064
BE 091-41-5: with PDV 0331/PDV 0346 (ABCR), i.e., polydimethyl siloxanes with terminal vinyl groups with contents of 3.0-3.5 Mol-% diphenyl siloxane units in the chain with viscosities of 1 Pas, or 60 Pas
* fertile microorganisms could not be determined

The invention claimed is:

1. Process for the sterilization and/or germ reduction of elastomeric two-component dental molding materials, said process comprising the steps of:
   providing two components of the dental molding materials, wherein at least one component of the two components comprises a polymer having one or more functional groups, and further wherein the at least one component comprises:
   i) silicone impression materials which are cross-linkable via addition curing or condensation curing reactions;
   ii) polyether impression materials which are cross-linkable via addition curing or condensation curing reactions or via a cross-linking ring-opening reaction;
   iii) ring opening polyether impression materials via an aziridino group;
   or
   iv) polyether impression materials which are cross-linkable by condensation reaction; and
   subjecting the two components in an unmixed state in a primary packing agent to radiation sterilization.

2. Process according to claim 1, wherein the two components are cross-linkable together.

3. Process according to claim 1, which further comprises radiation sterilizing, in addition to said dental mold materials, an addition cross-linking silicon impression material, said addition cross-linking silicon impression material comprising vinyl-group-containing polysiloxanes, said vinyl-group-containing polysiloxanes comprising at least in part diphenyl siloxane- and/or phenyl methyl siloxane structural units.

4. Process according to claim 3, wherein the addition cross-linking silicon impression material comprises a polymer comprising at least 3 Mol-% diphenyl siloxane and/or phenyl methyl siloxane units.

5. Process according to claim 4, wherein the polymer comprises at least 10 Mol-% diphenyl siloxane and/or phenyl methyl siloxane units.

6. Process according to claim 1, wherein the two components are arranged in the primary packaging and are simultaneously radiation treated along with accessories for mixing or for application of the dental molding material.

7. Process according to claim 1, wherein a twin-chamber cartridge is used as primary packaging and a mixing nozzle as accessory.

8. Process according to claim 1, wherein the radiation sterilization is performed by means of gamma rays or electron rays.

9. Process according to claim 8, wherein the radiation sterilization is performed at a radiation dose of a maximum of 50 kGy.

10. Process according to claim 9, wherein the radiation sterilization is performed at a radiation dose of 20 to 30 kGy.

11. Process according to claim 1, wherein the one or more functional groups is a vinyl group and a SiH group when the at least one component comprises silicone impression materials or an aziridino group when the at least one component comprises polyether impression materials.

* * * * *